United States Patent [19]

Deutsch et al.

[11] Patent Number: 4,489,054
[45] Date of Patent: Dec. 18, 1984

[54] CATIONIC LIPOPHILIC COMPLEXES OF $^{99m}$TC AND THEIR USE FOR MYOCARDIAL AND HEPATOBILIARY IMAGING

[75] Inventors: Edward A. Deutsch, Cincinnati; Kenneth A. Glavan, Poland, both of Ohio

[73] Assignee: Research Corporation, New York, N.Y.

[21] Appl. No.: 484,839

[22] Filed: Apr. 14, 1983

Related U.S. Application Data

[62] Division of Ser. No. 141,618, Apr. 18, 1980, Pat. No. 4,387,087.

[51] Int. Cl.$^3$ .................. A61K 43/00; A61K 49/00
[52] U.S. Cl. .................................... 424/1.1; 424/9; 260/429 J; 260/440
[58] Field of Search ............... 424/1.1, 9; 260/429 J, 260/440

[56] References Cited

U.S. PATENT DOCUMENTS

| | | | |
|---|---|---|---|
| 3,902,849 | 9/1975 | Barak et al. | 424/1.1 |
| 3,928,552 | 12/1975 | Winchell et al. | 424/1.1 |
| 3,961,038 | 6/1976 | Benes | 424/1.1 |
| 4,017,596 | 4/1977 | Loberg et al. | 424/1.1 |
| 4,031,198 | 6/1977 | Jackson | 424/1.1 |
| 4,058,593 | 11/1977 | Nora | 424/1.1 |
| 4,086,330 | 4/1978 | Petkav et al. | 424/1.1 |
| 4,088,747 | 5/1978 | Hunt | 424/1.1 |
| 4,091,088 | 5/1978 | Hunt | 424/1.1 |
| 4,256,726 | 3/1981 | Kato et al. | 424/1.1 |
| 4,256,727 | 3/1981 | Triplett et al. | 424/1.1 |

OTHER PUBLICATIONS

Fergusson et al., Chemistry and Industry, 3/26/60, pp. 347–348.
Thomas, et al., J. Am. Chem. Soc. 101 (8/16/79), pp. 4581–4585.
Robinson et al., J. Null. Med., 16: 561–562 (1975).
Firnav, Eur. J. Null. Med., 1: 137–139 (1976).
Loberg et al. Int. J. Appl. Rad. Isot., 29: 167–173 (1978).
Fergusson et al., Nature, 183: 1039–1040 (4/11/59).
Kubiatowitz et al., J. Pharmaceut. Sci., 68: 621–623 (1979).
Schubert, Scientific American, 214: 40–50 (1966).
Loberg et al., Abstract Reproduction Form, Soc. Nucl. Med., 23rd Annual Meeting, 1976.
Harvey, J. Nucl. Med., 20: 310–313 (1979).

*Primary Examiner*—Christine M. Nucker
*Attorney, Agent, or Firm*—Scully, Scott, Murphy & Presser

[57] ABSTRACT

A method of imaging organs with $^{99m}$Tc radiopharmaceuticals, especially of hepatobiliary imaging and negative myocardial infarct imaging in a mammal which comprises administering to the mammal a hepatobiliary or myocardial imaging amount of a cationic lipophilic complex of Tc-99m and detecting the Tc-99m complex in the mammal. A method for the preparation of cationic lipophilic complexes of Tc-99m.

24 Claims, 4 Drawing Figures

CATIONIC LIPOPHILIC COMPLEXES OF $^{99m}$TC AND THEIR USE FOR MYOCARDIAL AND HEPATOBILIARY IMAGING

Part of the work leading to the present invention was funded by the U.S. Department of Health, Education and Welfare; the U.S. Government is granted a royalty free non-exclusive license.

This is a division of application Ser. No. 141,618, filed Apr. 18, 1980, now U.S. Pat. No. 4,387,087.

BACKGROUND OF THE INVENTION

1. Field of the Invention

The present invention relates to cationic lipophilic complexes having utility as myocardial and hepatobiliary imaging agents.

2. Description of the Prior Art

In recent years diagnostic nuclear medicine has proven to be of enormous value to the medical community. Procedures for imaging, and therefore detecting abnormalities in the brain, liver, lungs, bones, and the like, have been well developed and are routinely used. These procedures are based on the tendency of the body to concentrate some chemical form of a particular gamma ray emitting isotope in the organ of interest; subsequent scanning of the organ with a gamma ray camera provides an image of the organ from which diagnostic information can be obtained. It is clear that the radioisotope with optimum nuclear properties (half-life, gamma ray energy, and the like) for medical gamma ray scanning is $^{99m}$Tc. It is therefore desirable to develop various chemical forms of Tc that will (a) concentrate in organs for which no satisfactory imaging agent has yet been found and/or (b) show greater organ specificity than the imaging agents currently available.

The metastable isotope Tc-99m has a 6 hour half-life and an emission spectrum, 99% gamma radiation at 140 KeV, which is well suited for techniques of diagnostic nuclear medicine. Tc-99m has a high specific activity, $5.28 \times 10^9$ millicuries per gram and a convenient rapid rate of decay; whereas its daughter product, Tc-99, has a specific activity which is almost 9 orders of magnitude lower and a half-life which is roughly 8 orders of magnitude longer. In recent years, Tc-99m has become readily available in hsopitals through the use of selective elution from a so-called molybdenum-99 (Mo-99) generator. The isotope Mo-99 produces Tc-99m as a radioactive decay product. (See for example, Jackson et al, U.S. Pat. No. 4,031,198, column 1).

The lack of efficaceous 99m-Tc myocardial imaging agents is probably the most important problem facing nuclear medicine today. Agents capable of visualizing myocardial infarcts would be especially useful in the clinic. There are two types of myocardial imaging agents: (1) The "positive" agents which accumulate in the infarcted area and therefore visualize the infarct as a "hot" spot of radioactivity on a relatively "cold" background of normal tissue. There are several "positive" 99m-Tc agents in current use, including 99m-Tc-pyrophosphate and 99m-Tc-HEDP; (Poe, N. D., Semin. Nucl. Med 7, 7-14 (1977): Buja, L. M. et al, J. Clin. Invest. 60. 724-740 (1977); Davis, M. A., et al, J. Nucl. Med., 17, 911-917 (1976); Wakat, M. A., et al, ibid, 21, 203-306 (1980)); (2) The "negative" agents which accumulate in the normal heart and therefore visualize the infarct as a "cold" area on a relatively "hot" background of normal tissue. There is currently no 99m-Tc "negative" imaging agent available. The agent used clinically is 201-Tl which is expensive, has a photo-peak that is low for optimum imaging, and provides a low count rate per dose. The replacement of 201-Tl with a 99m-Tc agent is a major quest in nuclear medicine.

The use of 99m-Tc radiopharmaceuticals for hepatobiliary imaging is well known in the art. By hepatobiliary imaging agent is meant a radiopharmaceutical which clears the bloodstream after a few minutes, accumulates in the liver and is subsequently secreted by the liver into the bile, gallbladder, common bile duct, and intestines. There has been a strong belief in the art that efficient hepatobiliary imaging agents have to be anionic. Thus, Firnau (European Journal of Nuclear Medicine, vol. 1, 137-139 (1976)) reviewed several references which disclose Tc-99m hepatobiliary imaging agents, and concluded that an absolute structural requirement for a substance to be excreted by the liver is that it be an organic anion. Firnau states that the reason for gallbladder and bile duct imaging in the Tc-99m chelates of the prior art, is their ability to quickly pass through the liver, this ability being rather unspecific and common to all organic anions.

This prejudice in the art towards the use of anionic lipophilic complexes of 99m-Tc appears to be born out by other work in this area. Loberg et al, U.S. Pat. No. 4,017,596 disclose liver-clearing chelates of 99m-Tc, wherein the chelating agents are substituted iminodiacetic acids and 8-hydroxyquinolines. These complexes are anionic. Loberg et al (International Journal of Applied Radiation and Isotopes, 1978, vol. 29, pp. 167-173) disclose technetium 99m-labeled N-(2,6-dimethyl-phenylcarbamoyl methyl)-iminodiacetic acid (Tc-HIDA) and its potential use as a radiopharmaceutical. Loberg et al (in Abstract: Society of Nuclear Medicine, 23rd Annual Meeting, 1976) demonstrate that this Tc-HIDA is an anionic monomer containing two HIDA ligands per Tc center. Winchell et al, U.S. Pat. No. 3,928,552 disclose a hepatobiliary radiopharmaceutical comprising 2-mercaptoisobutyric acid, chelating reduced technetium-99m. The aforementioned review article by Firnau (Eur. J. of Nuclear Medicine, 1, 137-139 (1976)) indicates that this radiopharmaceutical of Winchell et al is anionic. Jackson et al, U.S. Pat. No. 4,031,198 disclose a radiopharmaceutical for imaging the liver, labeled with technetium-99m, which includes a complexing agent which is a lipophilic mercaptan or thioketal. The mercaptan or thioketal complexes in this reference fall within the general type of anionic complexes discussed in the aforementioned Firnau review article.

Hunt et al, U.S. Pat. Nos. 4,088,747 and 4,091,088 discuss phenolic aminocarboxylic acid-liganded radiopharmaceuticals of technetium-99m. These phenolate/-carboxylate type of ligands are known to be anionic, and the resulting pharmaceuticals of 99m-Tc fall within the general type of the review article by Firnau.

From this brief review of the prior art, it can be concluded that hepatobiliary imaging agents of technetium-99m currently in clinical use have anionic character. Because of this property however, they all suffer from a serious deficiency. High levels of bilirubin reduce, or eliminate, the ability of anionic agents to image the hepatobiliary system. Harvey, L. et al, J. Nucl. Med., 20, 310-313 (1979) have recently shown that this is because bilirubin is also anionic and therefore at high concentrations, it blocks the anion clearance mechanism of the liver and prevents anionic imaging agents from accumulating in the liver. This is a serious clinical problem since many jaundiced patients, with obvious hepatobiliary malfunction, have high bilirubin levels and therefore cannot be successfully imaged with anionic agents.

Nora, U.S. Pat. No. 4,058,593 provides the only example of a cationic radiopharmaceutical based on technetium-99m which accumulates, albeit to a very small extent, in the liver. Nora discloses bone-specific radiopharmaceuticals based on technetium-99m with a complexing agent selected from the group of stannous fluoride, metal triflurostannate and metal pentafluorodistannate. These agents however, are not lipophilic, and act predominantly by mechanical deposition in the liver. The agents are not hepatobiliary imaging agents since they do not clear the liver and are not secreted therefrom into the bile, gallbladder, common bile duct, and intestines. Thus, the liver deposition observed by Nora would be insufficient to obtain good hepatobiliary imaging.

A need therefore, continues to exist for myocardial imaging agents based on Tc-99m, especially so-called "negative" myocardial infarct imaging agents. A need also continues to exist for cationic complexes of Tc-99m which will deposit in the liver and will be secreted therefrom, thus providing efficient hepatobiliary imaging.

SUMMARY OF THE INVENTION

It is therefore an object of the invention to provide cationic lipophilic Tc-99M radiopharmaceuticals for use in nuclear medicine.

Another object of the invention is to provide cationic lipophilic complexes of Tc-99m for hepatobiliary imaging, and for negative myocardial infarct imaging.

Still another object of the invention is to provide a method for myocardial and hepatobiliary imaging by using cationic lipophilic complexes of Tc-99m.

A further object of the invention is to provide a process for the preparation of cationic lipophilic complexes of Tc-99m.

These and other objects of the invention have been attained by providing:

A method for negative myocardial infarct imaging in a mammal which comprises:
  administering to said mammal a myocardial imaging amount of a cationic lipophilic complex of Tc-99m, and
  detecting said Tc-99m complex in said mammal.

Another object has been attained by providing a method for hepatobiliary imaging in a mammal which comprises:
  administering to said mammal a hepatobiliary imaging amount of a cationic lipophilic complex of Tc-99m, and
  detecting said Tc-99m complex in said mammal.

Other objects have been attained by providing cationic lipophilic complexes of 99m-Tc, as well as a process and kit useful for their preparation.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
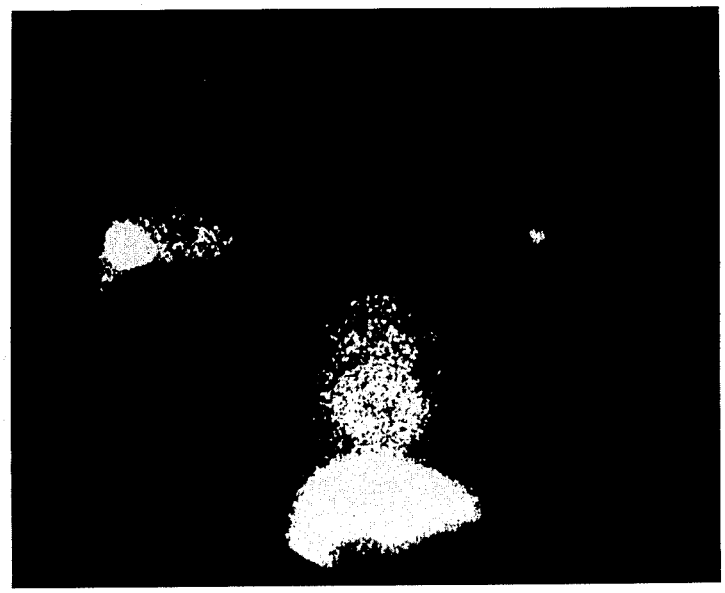
FIG. 1 shows a scanning photographic anterior image of a mongrel dog, 30 minutes post injection of 99m-Tc $(diars)_2Br_2^+$, where diars=o-phenylenebis(dimethylarsine).

The present invention provides cationic lipophilic complexes of 99m-Tc for imaging in nuclear medicine. These complexes are useful for negative myocardial infarct imaging, for hepatobiliary imaging, for pancreas imaging, and potentially for the imaging of other organs, such as the brain, lungs, kidney and the like.

The complexes of the present invention are particularly useful for negative myocardial infarct imaging. These are the first 99m-Tc myocardial imaging agents which accumulate in the normal heart and visualize the infarct as a cold area on a relatively hot background of normal tissue. As such, they are an optimal replacement for $201\text{-}Tl^+_{aq}$, the agent presently in use. They provide a rapid and safe diagnostic technique to determine if infarction has occurred, and to assess the extent and location of the disease. They show specificity for viable myocardial tissue relative to ischemic tissue, and non-viable myocardium, as well as surrounding organs. They rapidly clear from the blood in order to provide low background. Furthermore, by varying the chelating agent of the $^{99m}Tc$ center, it is possible to vary the rate of clearance of the complexes, and permit studies which are not possible with 201-Tl (e.g., serial scanning). 201-Tl clears at a specific, unique rate which cannot be varied.

The present invention also provides cationic lipophilic complexes of 99m-Tc as true hepatobiliary imaging agents. It has come as a great surprise to the present inventors to discover that cationic complexes of Tc-99m are capable of imaging the hepatobiliary system. This discovery goes against the general understanding and prejudice of the prior art. As stated previously, Firnau (Eur. J. of Nuclear Medicine, vol. 1, 137–139 (1976)) delineated the structural requirements for substances that serve as hepatobiliary imaging agents. Among them, it was believed that only organic anions would be able to quickly pass through the liver and image the gallbladder and bile ducts. Without being bound by any particular theory, Applicants believe that they have discovered that a cationic clearing mechanism of the liver is capable of clearing cationic lipophilic complexes of 99m-Tc. This directly contradicts the teachings of the prior art. The discovery of cationic imaging agents for the hepatobiliary system, opens up the possibility of treating patients with severe jaundice having high bilirubin levels, and which could heretofore not be imaged with the standard prior art anionic complexes.

By "cationic lipophilic complexes" is meant complexes of 99m-Tc having lipophilic ligands and an overall cationic charge. The cationic charge on the overall complex can be readily determined by evaluating its migration on an electrophoresis apparatus, or evaluating its absorption properties on cationic ion exchange resins or other absorption materials.

The term "lipophilic" as used in the invention implies that the ligands and complexes derived therefrom range from being purely lipophilic to having a balance of hydrophilic and lipophilic character. The term therefore encompasses solubilities which range from exclusive solubility in non-polar, water-immiscible organic solvents, to complexes having solubility both in these solvents and aqueous solvents. At the other extreme, are the non-lipophilic or hydrophilic cationic complexes, which are soluble exclusively in aqueous or polar organic water miscible solvents. It has been discovered that the cationic, highly lipophilic complexes of Tc-99m are excellent hepatobiliary imaging agents, rapidly clearing the bloodstream and the liver and depositing in the gallbladder, bile ducts and intestines. On the other hand, lipophilic cationic complexes having a balance of lipophilicity and hydrophilicity, and being soluble both in aqueous and non-aqueous, non-polar solvents are excellent imaging agents for the myocardium. Purely hydrophilic cationic complexes of technetium 99m, on the other hand, do not show any hepatobiliary imaging properties; they are rapidly cleared through the kidney. In summary, the complexes of the present invention range from being purely lipophilic to having a balance of lipophilicity and hydrophilicity, the latter having solubility in water and in non-polar, water-immiscible solvents.

The gradation of lipophilicity of the complexes of the present invention can be established by reference to partition coefficients using n-octanol/water, or n-octanol/buffer, or n-octanol/saline (King and Blau, J. Nucl. Med., 21, 147–152 (1980); Oldendorf, ibid, 19, 1182 (1978) and Proc. Soc. Exp. Biol. Med., 147, 813–816 (1974)). In general, those cationic lipophilic complexes of Tc-99m having n-octanol/saline partition coefficients greater than about 0.05 are useful in the present invention.

Among the preferred cationic lipophilic complexes of the invention are those having the formula:

$$[L_2^{99m}TcX_2]^+ X^-. \quad (I)$$

In this formula, L represents a lipophilic ligand strongly chelating for a Tc-99m cation wherein both L's may be the same or different, and X is an easily replaceable monovalent anionic ligand, wherein the three X's may be the same or different.

L has the general formula:

$$[A]\text{---}(Y:)_n \quad (2)$$

wherein n=2–5, preferably 2 or 3;

wherein A represents an alkylene lipophilic radical, or a monocyclic or polycyclic cycloaliphatic or aromatic lipophilic radical which may optionally be heterocyclic by containing in the ring or rings thereof, an atom selected from the group consisting of N, O, P, S or B. Most preferably, A is a lower alkylene radical, or A is a monocyclic or polycyclic aromatic radical. A may further be substituted, when necessary to increase the hydrophilic character of the molecule, with water solubilizing neutral groups such as hydroxy groups, thiol groups, carbonyl groups, and the like.

Y: is a neutral functional group having a free electron pair, capable of complexing with a Tc-99m cation having oxidation states less than +VII, preferably ranging from +I to +V. Thus, Y: may either be $Y^1R_2$ or $Y^2R$. $Y^1$ may be selected from the group consisting of N, P, As, Sb, or Bi. $Y^2$ can be selected from the group consisting of O, S, Se or Te. R is hydrogen or a $C_1$–$C_{15}$ straight or branched chain alkyl group. R may be unsubstituted or be substituted along the hydrocarbon chain with oxygens, nitrogens, sulfurs, or phosphorus, to thereby control the lipophilicity of the Tc-99m complex.

Among the preferred lipophilic ligands L are the following:

DMPE (($CH_3$)$_2$P—$CH_2CH_2$—P($CH_3$)$_2$);

diars (o-$C_6H_4$(As($CH_3$)$_2$)$_2$;

diphos (($C_6H_5$)$_2$P—$CH_2CH_2$—P($C_6H_5$)$_2$);

tris (1-pyrazolyl)borato;

porphyrin;

tetraphos P($CH_2CH_2$P($C_6H_5$)$_2$)$_3$;

DAE (($C_6H_5$)$_2$As—$CH_2CH_2$As($C_6H_5$)$_2$;

DIEN ($H_2$N—$CH_2CH_2$NHCH$_2$CH$_2$NH$_2$);

PPN (RN(CH$_2$CH$_2$P($C_6H_5$)$_2$)$_2$,

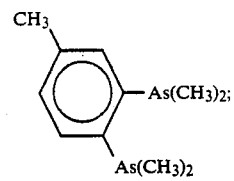

where R=H unsubstituted $C_1$–$C_{15}$alkyl; or $C_1$–$C_{15}$alkyl substituted by polar functional groups capable of rendering the resulting radical R with a wide range of hydrophilicity. A preferred series of Radicals R are those described in: Nozzo et al, J. Amer. Chem. Soc., 101 3683(1979) and Wilson et al, ibid, 100, 2269(1978), which are hereby incorporated by reference;

DMG (HO—N=C—C=N—O$^-$);
         |    |
        CH$_3$  CH$_3$

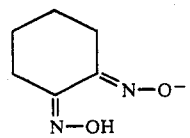

H$_2$P—CH$_2$CH$_2$PH$_2$;

H$_2$N—CH$_2$CH$_2$—SH;

-continued

H$_2$As—CH$_2$CH$_2$—AsH$_2$;

H$_2$N—CH$_2$CH$_2$—NH$_2$;

HS—CH$_2$CH$_2$—SH;

(CH$_3$)$_2$N—CH$_2$CH$_2$—N(CH$_3$)$_2$;

tris (1-pyrazolyl)methane;

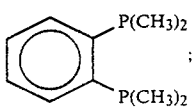

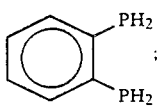

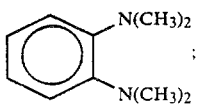

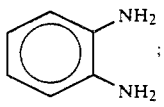

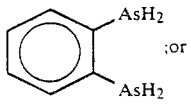

(CH$_3$)$_2$As—CH$_2$CH$_2$—As(CH$_2$)

As mentioned above, any ligand which would render the final 99m-Tc complex lipophilic, works in the present invention. The final 99m-Tc complex may thus be soluble in solvents ranging from oil-soluble solvents such as aromatic hydrocarbons, aliphatic or cycloaliphatic hydrocarbons, halogenated hydrocarbons, and the like, to more polar non-aqueous solvents such as alcohols or ketones. Among the aromatic hydrocarbons are benzene, toluene, xylenes, chlorobenzene, bromobenzene, and the like. Among the aliphatic hydrocarbons are pentane, hexanes, heptanes, octanes, decanes, and the like. Among the cycloaliphtic hydrocarbons are cyclopentane, cyclohexane, cyclooctane, etc. Among the halogenated hydrocarbons are chloroform, methylene chloride, carbontetrachloride, ethylene dichloride, and the like. Among the ketones are acetone, methyl ethyl ketone and the like. As mentioned previously, the term "lipophilic" as used in this invention, also includes solubility in both water and purely oil-soluble solvents.

X is a monovalent ligand which may be selected for example, from the group consisting of F$^-$, Cl$^-$, Br$^-$, I$^-$, SCN$^-$, N$_3^-$, CN$^-$, or RS$^-$. The latter thiol derivatives are especially important since the R group can be varied for chain length, steric bulk, electronic nature, charge and lipophilicity, vide supra.

In the cation [L$_2$ 99mTc X$_2$]$^+$, both X's, taken together may be part of a bidentate ligand capable of bridging cis coordination sites in a Tc-99m cation. Such ligands would include oxalate, HSCH$_2$CH$_2$SH, HSCH$_2$COOH, H$_2$N-CH$_2$CH$_2$-NH$_2$, and other derivatives using liganding functional groups such as HÓ, H , OOH, H$_2$, and the like. These ligands can also be substituted on the backbone to vary chain length, steric bulk, etc.

Among the preferred compounds for hepatobiliary or myocardial imaging are the 99m-Tc complexes derived from diars and tetraphos. The most preferred myocardial imaging agent is trans-99m-Tc (DMPE )$_2$Cl$_2^+$, and the most preferred hepatobiliary agent is $^{99m}$Tc(tetraphos)Cl$_2^+$.

The 99m-Tc lipophilic complexes of the present invention are prepared by novel techniques developed by the present inventors. Because of their short life (physical half-life of Tc-99m is 6 hours), the complexes must be manufactured near the place of use. The 99m-Tc isotope is produced by radioactive decomposition of its mother isotope, molybdenum Mo99. The isolation of the daughter isotope is in practice carried out with the aid of the so-called radionuclide generators, directly at the place where the material is to be used. The mother isotope, for example sodium molybdate or ammonium molybdate, is adsorbed on an adsorption column on a suitable carrier material, such as aluminum oxide, zirconium hydroxide or silica gel; the daughter isotope can be eluted by means of a suitable eluent and thus be separated from the mother isotope. When using a Mo-99 generator, the daughter isotope Tc-99m is eluted, for example, as pertechnetate (TcO$_4^-$) by means of physiological sodium chloride solution. The pertechnetate is then reduced from the +VII level to a lower valency level, preferably +I to +V, most preferably +III level, infra.

Normally, the eluates obtained from the generator and the solutions of derivatives which may subsequently be produced have a relatively low specific activity per volume (Tc-99m<5mCi/ml), though this suffices for static scintigraphy. For dynamic studies, to follow rapid functional sequences and for sequence scintigraphy, it is necessary to administer a high activity in as small a volume as possible. The detectors used are so-called scintillation cameras in combination with film recording or magnetic tape recording and computer evaluation. The specific activity per volume should be at least 10 to 15mCi/ml. To prepare such high specific activity solutions, prior art different methods can be used:

(1) The use of Mo99-Tc99m generators of high activity concentration (300–500 mCi). On fractional elution, these generators give, within the first few days, pertechnetate eluates of adequate specific activity per volume, namely 10-15mCi/ml. Upon preparation of reduced derivatives thereof, the specific activity per volume decreases due to dilution (Benes, U.S. Pat. No. 3,961,038, column 2);

(2) Extraction of an Mo99/Tc99m solution with methylethyl ketone, evaporation of solvent and solution of the residue in physiological sodium chloride solution (Journal of Nuclear Medicine, 11, 386 (1970));

(3) Contact of an aqueous solution of a 99m-Tc radionuclide of low specific activity with a metal hydroxide precipitate, separation of the precipitate with the radionuclide concentrated therein, and solution of the precipitate in an aqueous solution of a chelating agent (Benes, U.S. Pat. No. 3,961,038).

As mentioned above, Tc-99m is obtained from the generators in the form of a pertechnetate which has a relatively long dwelling time in human organs and because of this excessively long "biological half-life" is unsuitable for diagnostic applications. To manufacture the lipophilic complexes of the present invention, the pertechnetate is reduced. A number of reducing agents can be used for this purpose, and these are well known in the art. These reducing agents may include ascorbic acid, preferably in the presence of iron ions, sodium borohydride, Sn(II), or the use of the lipophilic chelating agent as the reducing agent per se. Other reducing metals such as ferrous, chromous, titanous and zirconyl ions can be used.

The essential aspects of the preparative methods developed by the present invention however, relate to the (a) complexation reaction of the lipophilic ligand on the 99m-Tc nucleus itself and (b) purification of the complex.

(A) Complexation Reaction. Because the pertechnetate or reduced derivative thereof (prepared by using one of the aforementioned reducing agents) is normally water soluble, and both the lipophilic ligand and final 99m-Tc complex may not be water soluble, it may be necessary to carry out the complexation reaction in a biphasic system.

When the ligand and final product are water soluble however, such a biphasic system is not necessary.

When using the biphasic system, the technetium starts out in the aqueous phase (as it is obtained from the Mo-99 generator) and is extracted into the non-aqueous phase during the preparation. The non-aqueous phase is necessary to dissolve the final product. Such biphasic complexation reactions can be carried out in a non-stirred or well-stirred condition. In the former case, the complexation reaction occurs at the interface and the final product diffuses into the non-aqueous phase. In the latter system, the reaction occurs in an "emulsion" with the product concentrating in the non-aqueous droplets. Any non-aqueous, water immiscible solvent may be used for such a biphasic complexation reaction. The previously listed water immiscible solvents (hydrocarbons and the like) are most preferred. The non-aqueous solvent should be capable of dissolving the lipophilic ligand used as starting material, and be capable of dissolving the final cationic lipophilic complex of Tc-99m. It should be easily separable from an aqueous solution by a standard separatory funnel-type separation. The final product should be easily obtainable therefrom by, for example, evaporation of the solvent.

The complexation reaction either in monophasic or biphasic systems, is carried out so that a large stoichiometric excess of lipophilic ligand is utilized over the stoichiometric amount of Tc-99m plus Tc99, present in the pertechnetate state or reduced state. Preferably, more than a tenfold excess of lipophilic ligand over 99m-Tc+99Tc is used.

The reaction is carried out over a wide range of temperatures, with a proviso that the aqueous phase and non-aqueous phase, if used) should remain liquid throughout the preparation. Thus, temperatures in the range of 0-80° C are normally used, most preferably 10-50° C.

The reaction times range from a few minutes to 1-2 hours. It should be recalled that the half-life of Tc-99m is only 6 hours and the reaction times have to be adjusted accordingly.

(B) Isolation and Purification of the Cationic Lipophilic Complexes. If a biphasic system is used, and after the reaction has come to a substantial completion, the aqueous phase and the non-aqueous phase are separated by standard physical methods such as utilization of a separatory funnel. It is possible at this stage to add excess non-aqueous solvent either of the same or different type than that used for the reaction, to further extract the aqueous phase. All non-aqueous phases are then combined and, if necessary the volume is reduced to a manageable level. The non-aqueous phase is then loaded on a chromatographic system which will adsorb cations and which is capable of separating cationic complexes from neutral or anionic molecules. In this manner, the cationic lipophilic complex of Tc-99m is adsorbed on the chromatographic material and purified from neutral unreacted ligand, or any other neutral or anionic impurity. When a single phase is used, the whole preparation can normally be loaded (after dilution) on the chromatographic material.

Among the preferred materials used for chromatography are alumina, silica, cationic exchange resins (styrene-based, cellulose-based, sugar-based, etc.), polyamide resins, cellulose resins, starch gel, and the like. After extensive washing with a non-eluting solvent, the cationic lipophilic complex is normally eluted with a polar organic solvent such as an alcohol, an amide, a ketone, or the like. For somewhat less lipophilic complexes, ion exchange chromatography is the most preferred method of purification.

After purification, as described above, the cationic lipophilic complex of Tc-99m is separated from the elution solvent if necessary, by rapid evaporation thereof. The complex is then dissolved or suspended in an appropriate pharmacologically acceptable administration medium.

Among the standard administration media, it is possible to use a vehicle which is saline, or 50/50 ethanol/saline (intravenous injection); vehicles wherein the concentration of ethanol is varied; vehicles wherein ethanol is replaced by other organic portions such as propylene glycol, glycerol, or dimethyl sulfoxide; or vehicles based on solubilization of the radiopharmaceutical in micelles. Nonionic surfactant emulsifying agents such as Tweens ® can be used in adminstering water insoluble radiopharmaceuticals (Risch et al in "The Chemistry of Radiopharmaceuticals", New York, Masson Publishers, 1978, pp. 123-154). Another method is to administer the complexes suspended or dispersed in water or aqueous solutions. This could be accomplished by dispersing the compounds via sonication, for example.

It is preferred to administer the radiopharmaceutical in a radioactive dose of from 0.01 mCi/ml to 10 mCi/ml, most preferably 2 mCi/ml-5 mCi/ml. The administration dose by weight of animal is 0.001 mCi/kg-1 mCi/kg; preferably 0.002 mCi/kg-0.1 mCi/kg.

Imaging of the myocardium or the hepatobiliary system can then be carried out (after waiting for appropriate periods of time to permit blood clearance of the radiopharmaceutical), by standard scanning techniques (Andres, J.T. et al, "Nuclear Medicine", Wiley & Sons, N.Y., 1977; "Basic Science Principles of Nuclear Medicine", Boyd, C. M. and Dalrymple, G. V., eds., Morby, St. Louis, 1974). For example, time dependent scintiscans of the chest region of a patient can be used. A computer interface, 16 crystal, Ohio Nuclear Spectrometer, is used for these scans and about 5mCi of a given radiopharmaceutical is injected; blood samples are concurrently collected via an indwelling intravenous catheter in order to determine blood clearance rates. Time dependent tissue distribution studies are then conducted.

The present complexes used for imaging the myocardium and the hepatobiliary system lend themselves to ready preparation, in a form which is compatible with a "kit" synthesis. A standardized kit preparation may involve a kit comprising a carrier being compartmented to receive a series of containers (vials; open ended tubes with or without stopper means at one or both ends; small bottles; and the like) in close confinement wherein one of the containers contains a 99mTc source, e.g. a standard Mo-99 molybdenum generator, and one or more containers might contain the particular lipophilic ligand by itself, or in combination with an appropriate reducing agent. These materials may be dissolved in an appropriate solvent or be provided solvent-free, with specific instructions. Pertechnetate from the generator is transferred into a container containing the ligand (and reductant, if one is used); after mixing and reaction for the specified time, the mixture is then passed through the appropriate chromatographic material having adsorbing capacity for cations. This material can be present in a third container which container is in the form of a short open ended chromatographic column; after passage therethrough, the 99m-Tc cationic complexes become absorbed on the chromatographic material. After rinsing with appropriate wash solvent, a displacement solution is then passed through the column to elute the desired radiopharmaceutical. In a preferred embodiment, such a kit would comprise a syringe fitted with a short cylindrical adapter capable of maintaining chromatographic material between the barrel of said syringe and the needle of said syringe (available commercially). This adapter contains the chromatographic material having adsorbing capacity for cations. After complexing the ligand on the 99m-Tc center (with concommitant reduction), the mixture is introduced into the barrel of the syringe. The mixture is ejected through the adapter containing the chromatographic material; the syringe is reloaded with wash solution which is ejected through the adapter; the syringe is then reloaded with displacement solution which is ejected through the adapter, removing the radiopharmaceutical into an appropriate container.

Preparations with such a kit may be completed anywhere between 15 minutes and 2 hours, thus making it a readily available and easily manageable procedure.

Having now generally described this invention, the same will be better understood by reference to specific examples, which are included herein for purposes of illustration only and are not intended to be limiting thereof.

EXAMPLE 1.

Preparation of trans-[Tc-99m(diars)$_2$Br$_2$]Br 10 ml of an aqueous alcoholic solution of HBr (a mixture of 6 M HBr and 95% ethanol in equal volumes), 5.0 ml of 99m-sodium pertechnetate (obtained from a molybdenum generator and diluted to 5.0 ml with saline), and 0.01 ml of ortho-phenylenebis(dimethylarsine) were added to a 25 ml Erlenmeyer flask equipped with a Teflon®-coated stirring bar. The mixture was stirred and heated on a hotplate for 30 minutes. The mixture was allowed to cool for 20 minutes at room temperature. 10 ml of methylene chloride was added to the flask and stirred for 20 minutes. The organic phase was separated using a separatory funnel and loaded onto a 0.7 cm × 3.0 cm alumina adsorption column prepared with methylene chloride and topped off with 1 cm of sand. The column was washed with 4-6 ml of methylene chloride and the +1 species was eluted with 95% ethanol. The eluate was collected in 1 ml fractions. Approximate yield was 65%.

EXAMPLE 2.

Preparation of [99m-Tc(DMPE)$_2$Cl$_2$]Cl

The following were added to a 25 ml Erlenmeyer flask equipped with a Teflon®-coated stir bar: 10.0 ml of 0.1 N aqueous alcoholic HCl, 0.5 ml of Na$^{99m}$TcO$_4$, and 0.5 ml of DMPE (Bis(1,2-dimethylphosphino)ethane). The mixture was stirred and heated at a boil for 30 minutes. After 15 minutes of stirring and heating, 5 drops of 3 M HCl were added to the flask. The mixture was cooled at room temperature for 15 minutes; it was then diluted to a volume of 50 ml with distilled water and loaded onto a SP-Sephadex C-25® ion exchange column (1.5 cm I.D.×7.0 cm) prepared with distilled water and layered with 1 cm of sand. The column was washed with 50 ml of distilled water and the cationic species subsequently eluted with normal saline. Yield is approximately 65%.

EXAMPLE 3.

Preparation of [99m-Tc(DMPE)$_2$Br$_2$]Br

The same procedure was followed as for Example 2, except for the following changes:

(1) 0.1 N aqueous alcoholic HBr instead of HCl;
(2) 30 drops of 3 M HBr were added after 15 min., instead of 5 drops of 3 M HCl;
(3) diluted to a total volume of 150 ml instead of 50 ml before loading onto the column;
(4) column: 1.5 cm I.D. x 10.0 cm;
(5) Yield was approximately 47%.

EXAMPLE 4.

Myocardial Imaging with trans-[Tc(diars)$_2$Br$_2$]Br

A normal mongrel dog was injected using a 50% ethanol/50% saline mixture as vehicle with the diars complex prepared in Example 1. Images of the dog were obtained with a high sensitivity colimator clearly visualizing the myocardium, with maximal myocardial uptake occurring about 20 minutes post injection. The bulk of the activity is taken out by the hepatobiliary system. Table 1, further shows the tissue distribution studies using normal female Sprague-Dawley rats.

TABLE 1

|  | Time post dose | | | |
| --- | --- | --- | --- | --- |
|  | 10 min | 30 min | 60 min | 120 min |
| Blood | 0.38(3)* | 0.27(3) | 0.21(1) | 0.18(3) |
| Heart | 2.3(5) | 1.8(1) | 1.3(1) | 1.0(1) |
| Liver | 4.5(6) | 2.9(6) | 2.7(3) | 2.1(2) |
| Pancreas | 1.0(3) | 1.2(2) | 0.9(1) | 0.8(1) |
| Kidney | 3.1(6) | 2.3(1) | 2.1(1) | 1.9(1) |
| Femur Muscle | 0.22(6) | 0.29(3) | 0.26(5) | 0.28(2) |

*Standard deviation of last significant digit given in parentheses.

The Table demonstrates that normal rats show significant myocardial uptake (2.3% of the dose/g inmyocardium at 10 minutes post injection).

EXAMPLE 5.

Myocardial Imaging Using [99m-Tc(DMPE)$_2$Br$_2$]$^-$

Myocardial uptake by the heart of a normal mongrel dog was observed with the title complex, under the same conditions as those for Example 4.

EXAMPLE 6.

Hepatobiliary Imaging Using trans-[Tc-99m(diars)₂Br₂]Br

The title complex was injected in the same vehicle as in Example 4 into a mongrel dog and images were obtained by positioning a camera directly over the chest of the dog. The following results were obtained.

0 minutes: Immediately after injection, most of the complex is in the blood pool which is predominantly in the heart chambers.

1 minute: One minute after injection, the complex begins to clear from the blood and starts to enter the liver. The gallbladder does not yet contain any activity.

5 minutes: The complex is all gone from the blood, the heart image has disappeared, and most of it is in the liver. A small amount has begun to enter the gallbladder.

10 minutes: The gallbladder has taken up most of the complex and appears brighter than even the liver.

Figure 2:
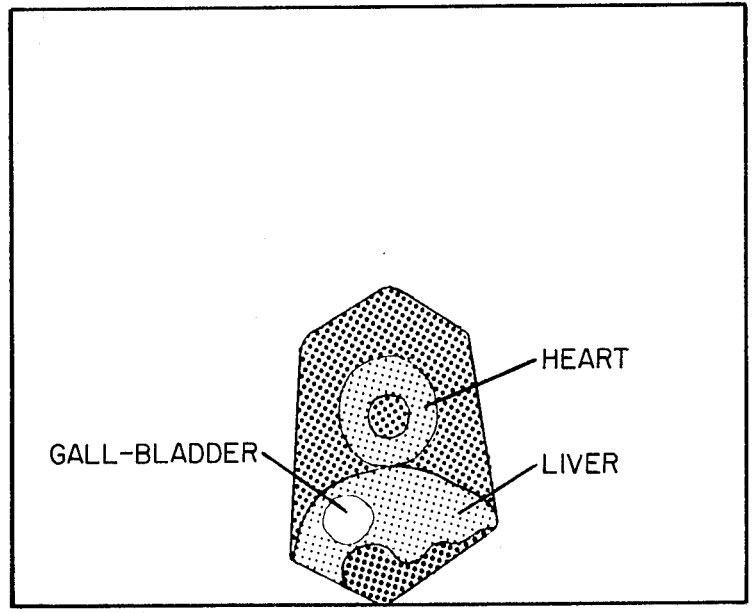
FIG. 2 is a schematic describing the photograph of FIG. 1. Both the photograph and accompanying schematic were taken after the complex had cleared the blood (5 minutes after injection), entered the liver and started clearing the liver and entering the gallbladder (10 minutes after injection). The picture is taken at the time when the gallbladder has taken up the bulk of the complex and the liver contains relatively little activity (30 minutes).

20 minutes: The gallbladder has taken up the bulk of the complex and the liver contains relatively little activity. FIGS. 1 and 2 demonstrate the image obtained after 30 minutes.

EXAMPLE 7.

Figure 4:
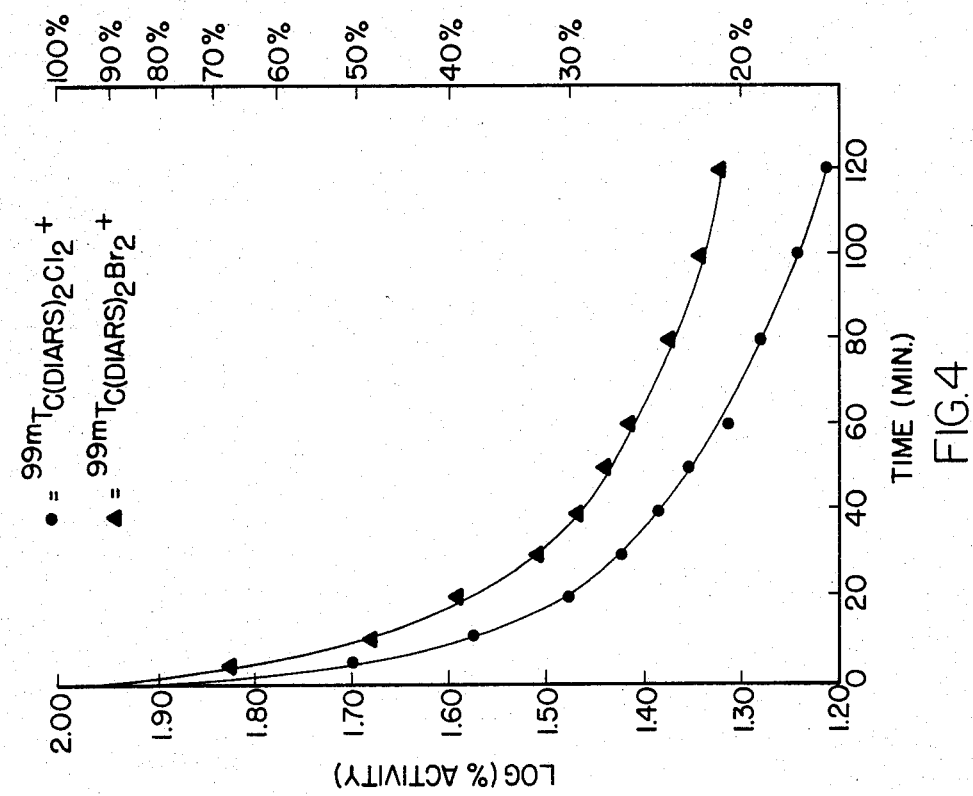
FIG. 4 shows the blood clearance curves for the two complexes of FIG. 3. It is clear that these two chemically similar agents are somewhat differentiated in the biological system.
Figure 3:
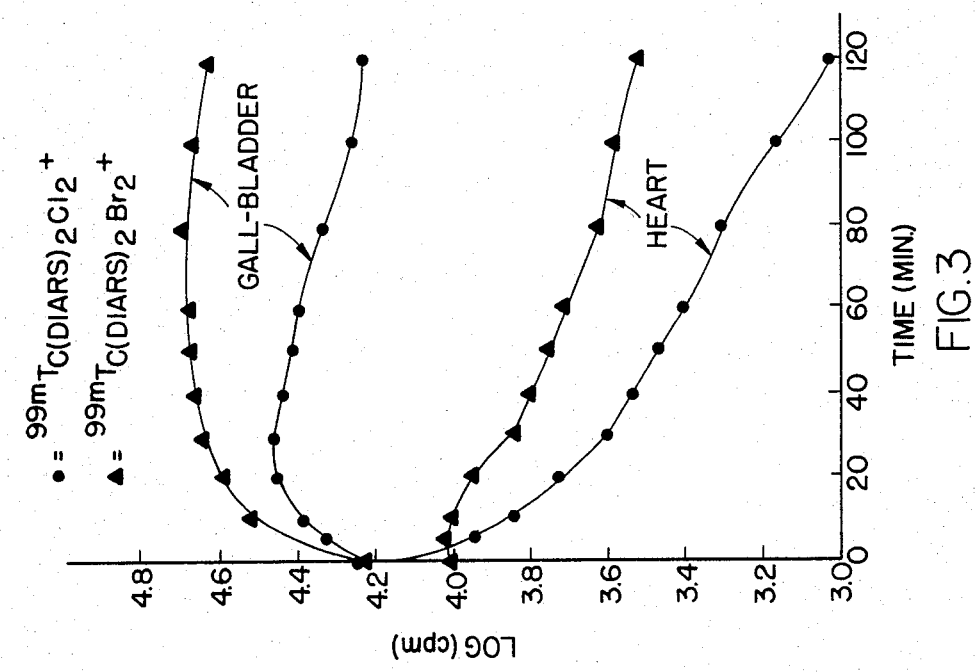
FIG. 3 compares the gallbladder uptake and heart clearing of 99m-Tc $(diars)_2Cl_2^+$ with that of 99m-Tc $(diars)_2Br_2^+$. Time dependent myocardial and gallbladder distributions obtained by computer analysis of scintigraphic data show that the chlorine complex clears from the heart more rapidly than the bromine complex, and that the gallbladder handles these two agents differently.

Comparison Between the Use of 99m-Tc (diars)₂Br₂⁺ and 99m-Tc (diars)₂Cl₂⁺ as Hepatobiliary and Myocardial Imaging Agents The two title complexes were injected into a dog as described for the complex of Example 4. Whereas with 99m-Tc (diars)₂Br₂⁺, the myocardium is readily visualized 20-40 minutes post intravenous injection, and gallbladder uptake is relatively slow, with the very similar complex 99m-Tc(diars)₂Cl₂⁺, the myocardium is imaged to a somewhat lesser degree and gallbladder uptake is rapid. These differences are graphically illustrated in FIG. 3, wherein are plotted time dependent myocardial and gallbladder distributions obtained by computer analysis of scintigraphic data; data for a given complex are normalized, but comparative data between complexes are not. From FIG. 3, it is seen that 99m-Tc (diars)₂Cl₂⁺ clears from the heart much more rapidly than 99m-Tc(diars)₂Br₂⁺ and that the gallbladder handles these two agents differently. Blood clearance curves for these two complexes are shown in FIG. 4, and again it is clear that these two chemically similar agents although being excellent imaging agents are biologically differentiated.

What is claimed as new and intended to be covered by Letters Patent of the United States is:

1. A cationic lipophilic complex of Tc-99m having an n-octanol/saline partition coefficient greater than about 0.05.

2. The complex of claim 1, which is soluble in nonpolar water immiscible solvents.

3. The complex of claim 2, which is also soluble in polar water-miscible solvents.

4. The complex of claim 1, which has the formula $$(L_2{}^{99m}TcX_2)^+X^-$$

wherein L is a polyvalent neutral lipophilic ligand which is strongly chelating towards a $^{99m}Tc$ cation;

X are the same or different monovalent anionic ligands; or, in the formula $(L_2{}^{99m}TcX_2)^+$, both X's are part of the same bidentate ligand capable of coordinating the cis positions of a $^{99m}Tc$ cation.

5. The complex of claim 4, wherein L has the formula $$[A]\text{---}(Y:)_n$$

wherein n=2-5;

wherein A is selected from the group consisting of a substituted or unsubstituted alkylene radical, a homomonocyclic or homopolycyclic lipophilic organic radical, and a heteromonocyclic or heteropolycyclic organic radical containing in at least one ring thereof an atom selected from the group consisting of N, O, P, S, or B;

Y: are the same or different neutral functional groups having a free electron pair capable of complexing with a $^{99m}Tc$ cation.

6. The complex of claim 5, wherein n=2 or 3.

7. The complex of claim 5, wherein A is -CH₂CH₂-.

8. The complex of claim 5, wherein Y: are the same or different functional groups selected from the group consisting of $Y^1R_2$ and $Y^2R$, wherein $Y^1$ is an atom selected from the group consisting of N, P, As, Sb, and Bi;

$Y^2$ is an atom selected from the group consisting of O, S, Se, and Te; and

R is selected from the group consisting of hydrogen, an unsubstituted $C_1$-$C_{15}$ straight or branched chain alkyl group, and a $C_1$-$C_{15}$ straight or branched chain alkyl group substituted along or on the hydrocarbon chain with oxygen, nitrogen, sulfur or phosphorous.

9. The complex of claim 5, wherein said ligand X's are the same or different ligands selected from the group consisting of F⁻, Cl⁻, Br⁻, I⁻, SCN⁻, N₃⁻, CN⁻, and RS⁻, wherein R is selected from the group consisting of an unsubstituted $C_1$-$C_{15}$ straight or branched alkyl group, and a $C_1$-$C_{15}$ straight or branched chain alkyl group substituted along or on the hydrocarbon chain with oxygen, nitrogen, sulfur or phosphorous.

10. The complex of claim 1, which is selected from the group consisting of ($^{99m}Tc(diars)_2Br_2$)Br and ($^{99m}Tc(diars)_2Cl_2$)Cl.

11. The complex of claim 1, which is selected from the group consisting of ($^{99m}Tc(DMPE)_2Br_2$)Br and ($^{99m}Tc(DMPE)_2Cl_2$)Cl.

12. The complex of claim 1, which is ($^{99m}Tc(tetraphos)Br_2$)Br.

13. The complex of claim 1 in combination with a pharmacologically inert vehicle.

14. The complex of claim 13, wherein said vehicle is 50:50 ethanol/saline.

15. A process of preparing a cationic lipophilic complex of $^{99m}Tc$ of the formula:

$$(L_2{}^{99m}TcX_2)X$$

wherein L is a neutral lipophilic ligand which is strongly chelating towards a $^{99m}Tc$ cation and which is capable of reducing $Tc^{+7}$ to a lower valence state;

X are the same or different monovalent anionic ligands, which comprises:

reducing a $^{99m}Tc^{+7}$ species to a lower valency state species with a ligand L, wherein the $^{99m}Tc^{+7}$ is present in an aqueous phase, wherein the ligand L is present in a water immiscible phase in intimate contact with said aqueous phase, and wherein during the reduction, said lower valency state species of $^{99m}$Tc is transferred to said non-aqueous phase.

16. The process of claim 15, wherein, after said transfer of said lower valency state species of $^{99m}$Tc into said water-immiscible phase, the process further comprises:
adsorbing said species in complexation with said ligand L, on a material having adsorbing capacity for cations, being capable of separating cationic complexes from neutral or anionic molecules and
eluting substantially pure $(^{99m}TcL_2X_2)^+$ species therefrom.

17. A kit comprising a carrier being compartmented to receive a series of containers in close confinement which comprises:
a first container containing a source of 99mTc;
a second container containing a polyvalent neutral lipophilic ligand L which is strongly chelating towards a $^{99m}$Tc cation which provides a cationic lipophilic complex of Tc-99m having an n-octanol/saline partition coefficient greater than about 0.05;
a third container containing chromatographic material having adsorbing capacity for cations.

18. The kit of claim 17, wherein said second container further contains a reducing agent capable of reducing $^{99m}$Tc from a valency state of +VII to a lower valency state.

19. The kit of claim 17, wherein said third container is in the form of a short chromatography tube.

20. The kit of claim 17, wherein said third container is in the form of a syringe adapter capable of maintaining chromatographic material between the barrel of said syringe and the needle of said syringe.

21. The kit of claim 20, wherein said kit also contains a syringe capable of fitting said adapter.

22. The kit of claim 17, wherein said chromatographic material is selected from the group consisting of alumina, silica and a cationic exchange resin.

23. The kit of claim 17 wherein said $^{99m}$Tc generator is a Mo-99 molybdenum generator.

24. A diagnostic product for hepatobiliary, myocardial, pancreas and brain imaging in a mammal comprising an imaging amount of a cationic lipophilic complex of Tc-99m according to claim 1.

* * * * *